United States Patent [19]

Murray et al.

[11] 3,965,899

[45] *June 29, 1976

[54] HYGIENIC DOUCHE SYSTEM

[76] Inventors: Jerome L. Murray, 652 First Ave., New York, N.Y. 10016; Frances R. Gardiner, 43 Park Road, Sparta, N.J. 07871

[ * ] Notice: The portion of the term of this patent subsequent to Sept. 4, 1990, has been disclaimed.

[22] Filed: Mar. 17, 1975

[21] Appl. No.: 558,954

Related U.S. Application Data

[60] Continuation-in-part of Ser. No. 382,658, July 26, 1973, Pat. No. 3,871,518, which is a division of Ser. No. 231,336, March 2, 1972, Pat. No. 3,756,236, which is a continuation-in-part of Ser. No. 197,848, Nov. 11, 1971, Pat. No. 3,756,230.

[52] U.S. Cl................................ 128/225; 222/397
[51] Int. Cl.$^2$........................................... A61M 3/00
[58] Field of Search ........... 128/225, 224, 222, 272, 128/251; 222/394–399

[56] References Cited
UNITED STATES PATENTS

| | | |
|---|---|---|
| 3,756,230 | 9/1973 | Murray et al. ...................... 128/225 |
| 3,756,236 | 9/1973 | Murray et al. ...................... 128/225 |
| 3,847,149 | 11/1974 | Murray et al. ...................... 128/225 |
| 3,871,518 | 3/1975 | Murray et al. ................... 128/225 X |

*Primary Examiner*—John D. Yasko
*Attorney, Agent, or Firm*—Curtis, Morris & Safford

[57] ABSTRACT

A hygienic douche apparatus including a nozzle for insertion into a vaginal passage and a cooperating fluid holding container are provided. The container includes a separate compartment therein to hold a compound which is soluble in a fluid such as water and, when dissolved, forms a hygienic douching fluid. The compound includes an ingredient which reacts with water to evolve a gas to pressurize the container and dispel the hygienic douching fluid through the nozzle. The compartment includes means operable from outside the container to initiate contact between the liquid and the compound. The apparatus is also adaptable to be used with an enema-type nozzle to provide a convenient readily dispensible enema and with a bidet nozzle to provide a convenient bidet apparatus.

8 Claims, 9 Drawing Figures

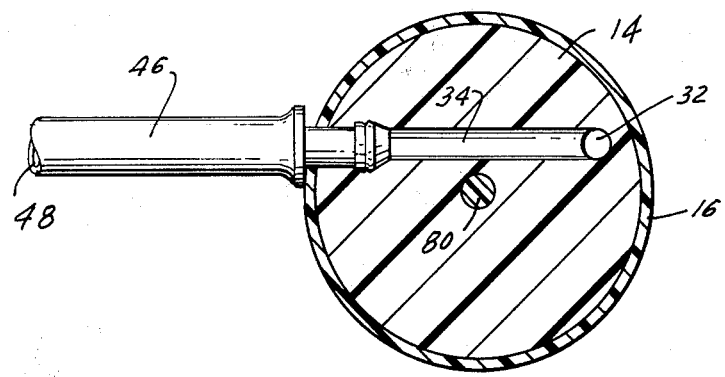
FIG. 5
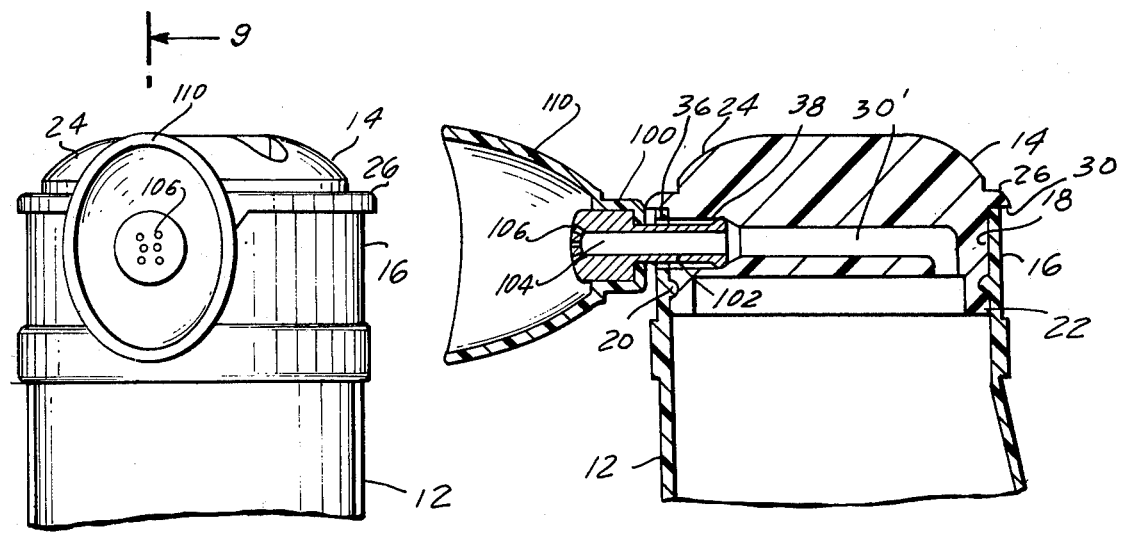
FIG. 8
FIG. 9

HYGIENIC DOUCHE SYSTEM

This application is a continuation-in-part of copending application Ser. No. 382,658, filed July 26, 1973, now U.S. Pat. No. 3,871,518, which application was a division of copending application Ser. No. 231,336, filed Mar. 2, 1972, now U.S. Pat. No. 3,756,236, which application in turn was a continuation-in-part of copending application Ser. No. 197,848, filed Nov. 11, 1971, now U.S. Pat. No. 3,756,230.

The present invention relates to hygienic douche systems and more in particular to an improved hygienic douche wherein the douching fluid is ejected from a nozzle at a controlled pressure which is generated within the system itself.

It has been found that the ideal pressure from the douche nozzle for most effective and safe cleansing action during douching should be maintained below about 2 p.s.i. and most preferably about 1 to 1.5 p.s.i. Pressures in excess of this may cause harmful bacteria which may be present in the vaginal area to be flushed into the uterus and may increase the chance of infection. Too much pressure may also cause physical damage as well. Consequently, it is recommended, when using the most popular type of douche apparatus, i.e., a bag to hold a douche solution with a tube leading from the bag to a nozzle, that the bag be held at shoulder height, approximately 23–24 inches from the nozzle. This results in a pressure head of about 1 p.s.i. However, it has been found, that due to the inconvenience of holding the bag at shoulder height when using a device such as this, most users hang the bag from the most convenient place available, which for a bathroom would be a shower rod, and thus develop a pressure head at the nozzle in excess of 2 p.s.i.

Other types of douche apparatus utilize a collapsible bag which is manually compressed by the user to create sufficient pressure on the douche solution in the bag to eject the solution through the nozzle. With this type of apparatus, the same difficulty is also encountered in that there is no control of the precise pressure which is developed and typically more than the desired 1 to 1.5 p.s.i. is developed by the user.

Similar problems are inherent in devices presently used to administer enemas in that enema administering devices also fail to provide an effective and safe method of controlling the pressure at which the enema solution leaves the enema nozzle.

In other types of douche apparatus, a pressurized container is utilized to eject the douche solution through a valve system leading to the ejection nozzle. While such devices are less cumbersome to use, no provision is made to control the pressure to a safe level and the valving systems are needlessly complex and expensive to manufacture.

Accordingly, it is an object of the present invention to provide a convenient, safe and effective apparatus which is adaptable to administer both douches and enemas and which may also be used as a bidet.

It is another object of the present invention to provide an apparatus to administer douches and enemas and to be used as a bidet in which the release pressure of the douche or enema solution is carefully maintained at a safe and effective level.

It is a further object of the present invention to provide an apparatus to administer douches and enemas and to be used as a bidet which is of simple and sturdy construction and of a convenient size for storage and ready use.

It is a still further object of the present invention to provide an apparatus to administer douches and enemas and to be used as a bidet which is exceedingly simple to use and which does not entail complicated or difficult procedures.

It is yet another object of the present invention to provide a hygienic douche apparatus to administer douches and which can be readily converted to a bidet apparatus by substituting a bidet nozzle for the douche nozzle.

These and other objects and advantages will be more readily apparent after consideration of the following specification and drawings:

FIG. 5 is a view taken along line 5—5 of FIG. 4;

FIG. 8 is an elevational view showing the device used as a bidet; and

FIG. 9 is a partial sectional view taken on line 9—9 of FIG. 8.

Figures 1, 2:
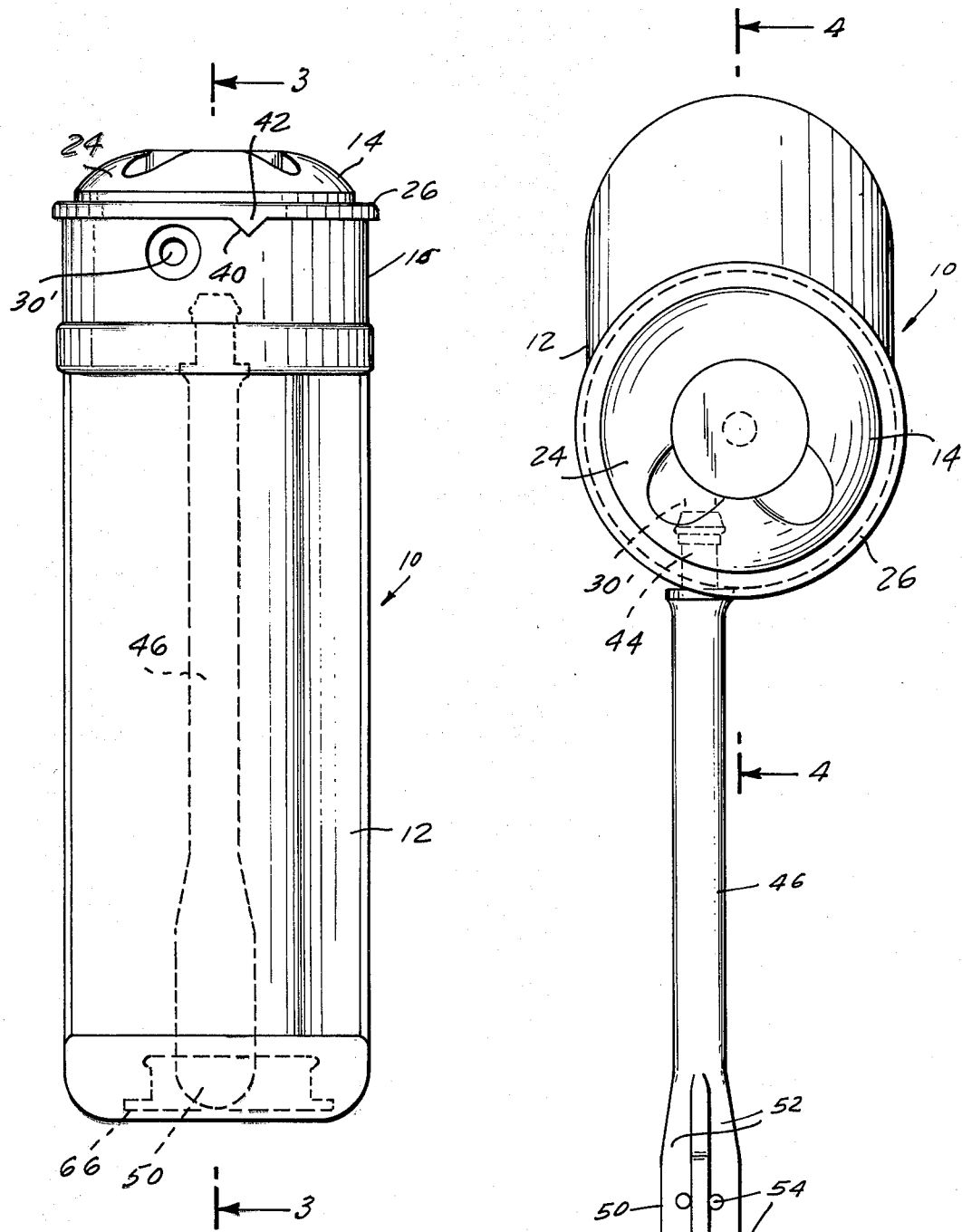
FIG. 1 is a front elevational view showing the apparatus of the present invention in a storage mode.
FIG. 2 is a top plan view showing the nozzle in position and the apparatus in a ready to use position.

With reference to the drawings and particularly FIGS. 1–7, there is shown the douche apparatus 10 of the present invention including an open top vessel or container 12, preferably of a molded plastic material, closed by a removable cap member 14. The container 12 includes a neck portion 16 which is open as at 18 and which is provided with an integral internal protuberance 20 having a semi-circular cross section about the inner circumference of the neck portion 16. Neck portion 16 and protuberance 20 cooperate with the lower portion 22 of cap member 14 so that cap member 14 fits within opening 18 by a liquid tight press fit.

The container 12 may be of any desired exterior shape for convenient storage. For the preferred embodiment of a douching or enema apparatus shown herein, dispenser container 12 may have an internal fluid capacity of approximately one pint although it is to be understood that any fluid capacity may also be provided if desired.

The cap member 14 is also preferably of a molded plastic material and includes an end wall 24 of sufficient axial length to fit into opening 18 for a significant extent. A flanged extension 26 is provided to cooperate with the end surface 28 of the neck of container 12. Thus, when the cap 14 is tightly engaged on container 12, the lower surface 30 of flange 26 abuts against the upper edge 28 of container 12 to seal the open top of the container and form a fluid tight barrier to retain liquid within container 12.

A fluid passage 30' is provided through the cap member 14 and is defined by longitudinally oriented cylindrical bore segment 32 which intersects with a transversely oriented cylindrical bore segment 34 communicating with a fluid outlet port 36 in the side of cap 14. Thus, fluid communication is provided between the exterior of the cap 14 and the interior of container 12.

A fluid outlet port 38 is provided in neck portion 16 of container 12 in register with fluid outlet port 36 of cap 14. To insure proper alignment of the cap and container, so ports 36 and 38 are in register, a notch 40 is provided on neck 16 and a complimentary protrusion 42 is provided on cap 14. Thus when protrusion 42 fits into notch 40 proper alignment is maintained.

In use, the shank portion 44 of a douche nozzle 46 fits tightly within and is snugly retained in outlet ports 36 and 38 so that a continuous fluid passage is provided from the interior of container 12 through the fluid outlet ports and through the nozzle 46. Nozzle 46 is of cylindrical construction and includes a central longitudinal fluid passage 48 extending through the shank and into a closed rounded end portion 50. Axial grooves 52 are provided near the end 50 in which are provided a plurality of outlet apertures 54 communicating with fluid passage 48 to allow douching solution to exit the nozzle. The end 56 of shank 44 includes a rounded protuberance 58 to insure a tight friction fit in outlet port 36 of cap 14.

To use the douche apparatus, cap 14 is placed on the container 12, nozzle 46 is inserted within outlet ports 36 and 38 so that a continuous fluid passage is provided from the interior of container 12 to the fluid outlet apertures 54 in the end portion of the nozzle. The shank 44 of the nozzle is adapted to fit snugly within the outlet ports and to be tightly retained therein to preclude leakage of fluid when the apparatus is in use.

Prior to placement of cap 14 on container 12, the container is filled with a suitable liquid, such as water, and cap 14 is reassembled so that the water within container 12 can react with a suitable compound which, when dissolved in water, provides an aqueous physiologically inert douche or enema solution. The compound also includes an effervescent ingredient to react with the water and generate a gas to pressurize the container to drive the fluid through the fluid passage within cap 14 and then through the nozzle 46 and out the fluid outlet apertures 54 therein.

Accordingly, a compound receiving chamber is provided which is initially sealed against the fluid within the container 12 but which can be selectively opened to allow the water within the container to react with the compound.

Thus, cap 14 is provided with a housing 60 below the underside 62 of wall member 24 of cap member 14. Housing 60 may be of any cross-sectional configuration but for the embodiment shown herein is preferably circular in cross-section and includes a depending side wall 64 terminating in an opening 65. Thus wall 64 and underside 62 of cap 14 within wall 64 define an ingredient receiving volume.

A removable cover 66 is provided to frictionally telescope within the open end 65 of housing 60 to seal the end of the housing when it is in place. Cover 66 is preferably of a pliable plastic material and is adapted to be manually placed over and removed from the open end of housing 60.

Cover 66 includes an end wall member 68 and an integral depending wall member 70 spaced radially inwardly from the outermost portion 72 of wall member 64 so that an overhanging flange portion is formed. Wall member 70 is dimensioned for sliding friction fit within housing 60.

Figure 6:
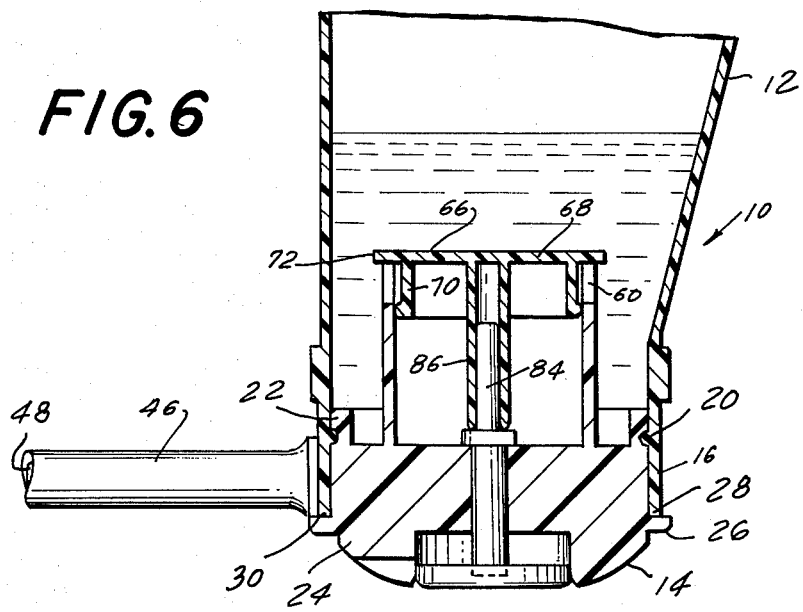
FIG. 6 is a fragmentary sectional view showing the device prior to activation.

Adjacent open end 65 of housing 60 a pair of diametrically opposed access slots 74 and 76, respectively, are provided. Slots 74 and 76 have an axial extent less than the axial extent of wall member 70 of cover 66 so that when cover 66 is assembled with the flanged portion abutting the end of wall 64 of housing 60, as shown in FIG. 6, a liquid tight seal is maintained. When cover 66 is moved away from housing 60, as shown in FIG. 7, access slots 74 and 76 are cleared so that fluid access between the interior of container 12 and the interior of housing 60 is provided.

Figure 7:
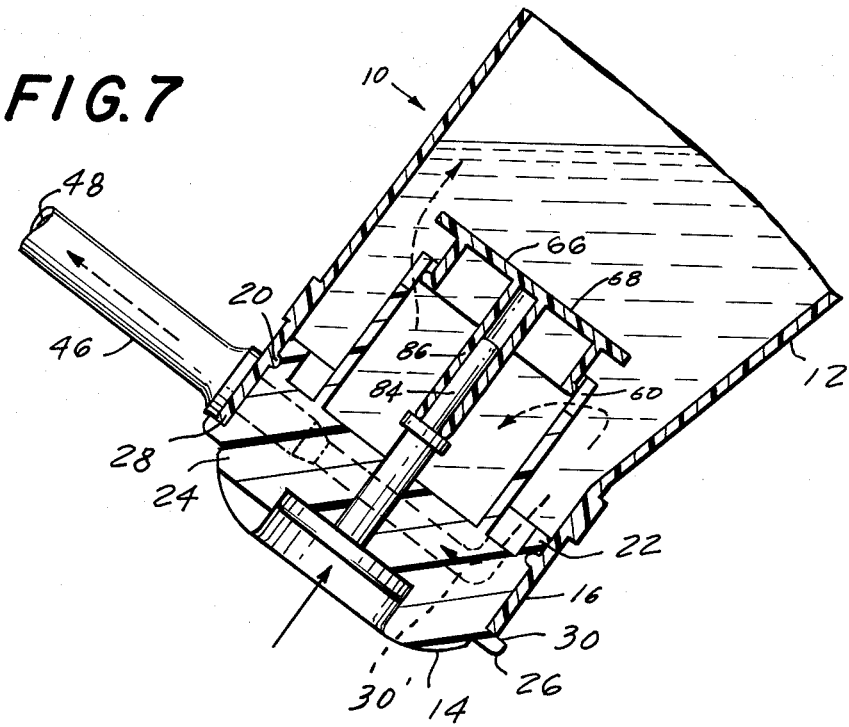
FIG. 7 is a view similar to FIG. 6 showing the device in an activated mode.

The cap 66 is movable from its fluid tight sealing position shown in FIG. 6 to the fluid access position shown in FIG. 7 from exterior container 12 by movement of a plunger assembly 78.

Plunger assembly 78 includes a rod like shaft member 80 slidably disposed within an access bore 82 through cap member 14. The end 84 of rod member 80 fits within a cylindrical segment 86 extending from end wall 68 of cover 60 and is frictionally retained therein. The other end 88 of rod member 80 which is disposed exterior container 12 is provided with a flanged contact button 90 which is disposed within a cutout segment 92 on the cap 14.

Thus when button 90 is depressed, rod 80 moves from the position shown in FIG. 6 to the position shown in FIG. 7 thereby to move cover 66 accordingly as well.

According to the present invention, the ingredients which when dissolved in a liquid such as water to form an aqueous solution are packaged in an envelope and are premeasured to react with a predetermined quantity of water, for example one pint of water. Included in the ingredients within the envelope is an ingredient to provide a cleansing action for douching or for use as a bidet and, also, an ingredient to provide an effervescent effect to build up the internal pressure within container 12 to completely eject the volume of liquid in the container through the nozzle 44. Necessarily, this ingredient releases a physiologically inert gas when reacted with water and the effervescent effect should preferably be sufficient to completely dispense the volume of water stored in container 12 and maintain between 1 to 1.5 p.s.i. pressure.

While it is to be understood that many ingredients may be selected to provide the cleansing function for douching, it has been found that granulated sodium bicarbonate is particularly effective as a light douche solution and anhydrous citric acid when dissolved in water in the presence of sodium bicarbonate has been found to be particularly effective to provide the effervescent effect. For the illustration of the present invention described herein, where the volume of water within container 12 is approximately one pint, it has been found that the combination of ingredients made up in the ratio of about 2.94 grams of sodium bicarbonate to 3.68 grams of citric acid provides a desirable and effective douche solution which releases gas when reacted in water to fully dispense one pint of water at the desired pressure and have sufficient gas pressurization to provide a gas "blow by" after all the fluid has been ejected from the container.

It has also been found that to avoid problems associated with compacting the two ingredients into a single tablet or capsule and also to prolong the shelf life of the compounds to avoid the propensity of the sodium bicarbonate to absorb moisture from the citric acid, it is best to segregate the sodium bicarbonate from the citric acid. Accordingly, preferably the envelope package containing the ingredients is provided with means to segregate one compound from the other and the ingredients are mixed when the envelope is emptied into housing 60.

To use the apparatus of the present invention, cap 14 is removed and the desired quantity of water placed in container 12. The ingredients are placed in housing 60, cover 66 is placed thereon in fluid tight position and is engaged on end 84 of rod 80. This moves rod 80 to the inactive mode with button 90 elevated with respect to cap 14. Cover 14 is placed on container 12 in proper alignment and nozzle 46 inserted in the outlet ports.

The device is now ready for operation and after nozzle 46 has been inserted in the vaginal canal button 90 is depressed to move cover 66 and allow the water to contact the ingredients in housing 60 to initiate effervescing and dispel the liquid solution.

Because the device 10 is held upside down at an angle, the water level in container 12 is disposed such that one of the access slots 74 is submerged in the water while the other 76 is open to the air in contaner 12. Such an orientation permits water flow into housing 60 and allows dispelling of the water from the opposite access slot after reaction with the ingredients within the housing as best shown in FIG. 7.

To insure this proper orientation access slots 74 and 76 are disposed in a plane parallel to a plane passing through the longitudinal axis of nozzle 46 when it is disposed in outlet ports 36 and 38.

Figure 3:
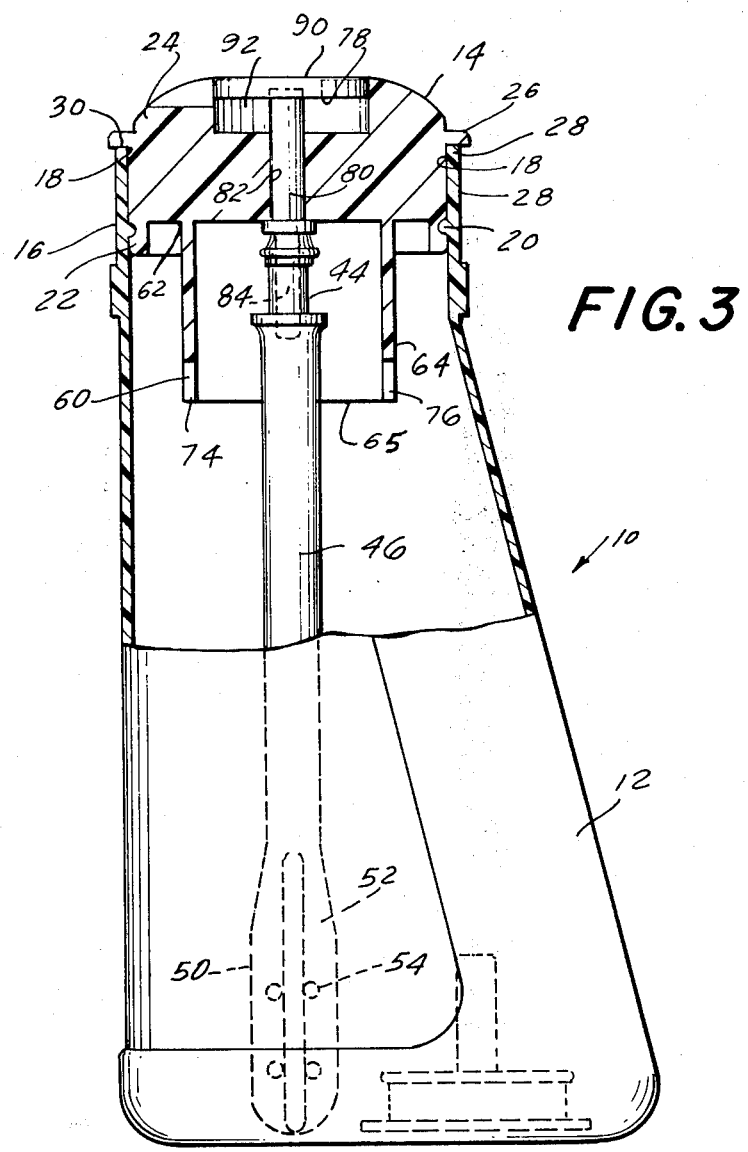
FIG. 3 is a partial sectional view taken on line 3—3 of FIG. 1.
Figure 4:
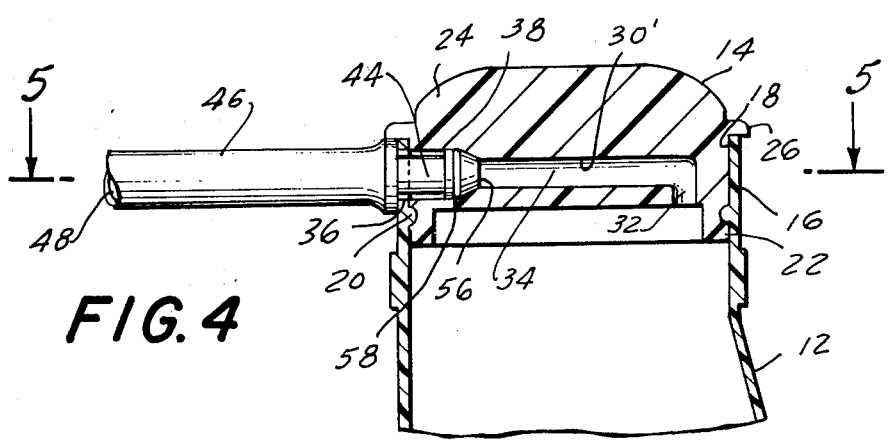
FIG. 4 is a partial sectional view taken along line 4—4 of FIG. 2.

Advantageously, as best shown in FIG. 3, cutout 92 in cap 14 has sufficient depth so that the upper surface of button 90 is disposed below the upper surface of cap 14. This insures that in placing cap 14 on container 12 button 90 may not be inadvertently depressed to activate the device unintentionally.

Accordingly, a pair of depressions 94 and 96 are provided, for either right or left hand use, in cutout 92 to permit placement of a finger therein to gain access to button 90 to depress the button when desired.

In addition, as shown in FIG. 3, container 12 and nozzle 46 are dimensioned so that in storage nozzle 46 may be maintained engaged on end 84 of rod 80 and cover 66 disposed within container 12.

As seen in FIGS. 8 and 9, the apparatus of the present invention may be used as a bidet device by the substitution of a bidet nozzle 100 for douche nozzle 46.

Bidet nozzle 100 includes a shank 102 having the same configuration as the shank of douche nozzle 46 for like insertion into outlet ports 36 and 38. A fluid passage 104 is provided through nozzle 100 and nozzle 100 includes an end wall 106 through which are disposed fluid access ports 108 to permit a spray of dispelled fluid to project. Fixed about shank 102 is a cup shaped member 110, preferably of a resilient composition, which acts as a constraining housing to direct fluid dispelled from ports 108 to the part of the body desired to be cleansed.

The present invention provides an apparatus to administer a hygienic douche, bidet or enema in a manner which is safe and simple and wherein the pressurization of the douche or enema solution can be controlled below a predetermined maximum level without requiring any attention or control of the user. In addition, the apparatus is convenient to use in that the apparatus may be prepared for use by enclosing a package of ingredients in a sealed chamber and no reaction occurs until the user activates the apparatus. Once activated the reaction proceeds rapidly and the full contents of the liquid container are dispelled without requiring any complicated valving or control by the user.

The insertion of nozzle end 44 through the outlet port 38 of container 12 and outlet port 36 of closure member 14 has an additional beneficial feature. When pressure is built up within container 12, the internal pressure causes a slight degree of relative movement between the cap and the container which causes a wedging locking action about the end of the nozzle to firmly and positively retain the nozzle in position to preclude nozzle removal even if pressure inadvertently builds up within container 12 to undesired levels. Thus safety in use is insured as the nozzle will not blow out even at unforseen and inordinately high internal levels.

While a preferred embodiment has been described herein in which an ingredient such as sodium bicarbonate to perform the cleansing function is included as part of the ingredients to be utilized in chamber 66 it is expressly understood that the cleansing ingredient could be omitted from the ingredients utilized in chamber 66 and a liquid solution of sodium bicarbonate or any other suitable physiologically inert solution may be added as a solution to container 12. In that event only one ingredient such as citric acid need be provided in chamber 66 to pressurize the container once contacted by the water to dispel the solution.

It is thus seen that an effective apparatus for administering a douche, enema or for use as a bidet has been provided which is extremely convenient and safe to use. The convenience is apparent as the device could be used in a shower or bath and the safety is assured as the maximum pressure build up is readily controlled.

What is claimed is:

1. A hygienic douche apparatus comprising:
    a container open at one end adapted to hold a quantity of liquid,
    a closure member for sealing said open end of said container,
    means defining a chamber within said container when said closure member is in sealing relationship on said container comprising a housing and a cover member therefor slidably disposed with respect to said housing and movable between a first sealed position and an unsealed second position,
    said chamber adapted to hold a predetermined quantity of a compound capable of generating gas pressure to dispel completely the said quantity of liquid from said container when said compound is contacted by said liquid,
    said cover member including means cooperable with said housing for sealing said chamber to preclude liquid contacting said compound in said chamber comprising cooperable means on said cover and said housing to effectively seal said chamber when said cover member is in said first position,
    means cooperable from the exterior of said chamber to move said cover member from said first position to said second position to cause liquid within said container to enter said chamber and to contact said compound and generate sufficient gas pressure within said container to dispel the quantity of liquid from said container, and
    means affording fluid communication between the interior of said container and the exterior for the passage of said quantity of liquid from said container after said compound is contacted by said liquid.

2. A hygienic douche apparatus as defined in claim 1 wherein said housing includes at least a pair of diametrically opposed fluid access ports therein, said access ports oriented within to be cooperable with said cover member for sealing said chamber whereby said access ports are sealed against fluid flow when said cover member is in said first position.

3. A hygienic douche apparatus as defined in claim 2 wherein said means cooperable with said housing for sealing said chamber comprises a segment of said cover member extending axially a sufficient length and telescoped within said housing to sealingly engage within said housing to seal said fluid access ports when said cover member is in said first position.

4. A hygienic douche apparatus as defined in claim 1 wherein said means operable from the exterior of said chamber to move said cover member from said first position to said second position comprises a rod member slidably disposed within said closure member and having one end in contact with said closure member and extending beyond said closure member whereby the exposed other end of said rod member may be depressed to move said cover member from said first position to said second position.

5. A hygienic douche apparatus as defined in claim 4 wherein said closure member includes a cutout portion therein about said exposed other end of said rod and the end of said rod is disposed therein below the exterior surface of said closure member to preclude inadvertent movement of said rod.

6. A hygienic douche apparatus as defined in claim 1 wherein said closure member is telescopically and sealingly disposed within said container open end and said means affording fluid communication between the interior of said container and the exterior comprises a fluid access passage through said closure member and said container.

7. A hygienic douche apparatus as defined in claim 6 including cooperable means on said closure and said container to align said closure and container to insure fluid communicating registry of said fluid access passages.

8. A hygienic douche apparatus as defined in claim 1 wherein said compound comprises a first ingredient soluble in water to form physiologically inert cleansing solution and a second ingredient soluble in water which generates a gas as it dissolves in a liquid in the presence of said first ingredient and wherein said first and second ingredients are packaged in predetermined quantities.

* * * * *